United States Patent [19]

Clark

[11] 4,262,253

[45] Apr. 14, 1981

[54] CONSTANT ALTERNATING CURRENT CONDUCTIVITY DETECTOR FOR A CHROMATOGRAPH

[75] Inventor: Vernon R. Clark, Bartlesville, Okla.

[73] Assignee: Phillips Petroleum Company, Bartlesville, Okla.

[21] Appl. No.: 900,406

[22] Filed: Apr. 26, 1978

[51] Int. Cl.³ .................. G01R 27/22; G01N 27/06
[52] U.S. Cl. .................................. 324/439; 324/442
[58] Field of Search .................. 324/30 R, 30 B, 13, 324/62, 65 R, 64, 71 CP, 324, 354, 355, 373, 442, 444, 439; 204/195 R

[56] References Cited

U.S. PATENT DOCUMENTS

| 2,712,628 | 7/1955 | Doll | 324/373 |
|---|---|---|---|
| 2,897,436 | 7/1959 | Douty | 324/442 |
| 3,105,190 | 9/1963 | Norris | 324/6 |
| 3,181,056 | 4/1965 | Boissonnas | 324/373 X |
| 3,235,793 | 2/1966 | Reese | 324/1 |
| 3,358,223 | 12/1967 | Birnstingl | 324/30 B |
| 3,430,129 | 2/1969 | Cardiero | 324/30 R |
| 3,430,130 | 2/1969 | Schneider | 324/30 R |
| 3,466,927 | 9/1969 | Magrini | 324/30 R |
| 3,531,252 | 9/1970 | Rivers | 324/30 R X |
| 3,558,280 | 1/1971 | Panson et al. | 324/30 X |
| 3,582,767 | 6/1971 | Brum et al. | 324/30 B |
| 3,748,899 | 7/1973 | Gregg et al. | 324/442 X |
| 3,831,083 | 8/1974 | Teass et al. | 324/30 R |
| 3,871,359 | 3/1975 | Pacela | 324/65 R X |
| 3,904,365 | 9/1975 | Larson et al. | 324/30 R X |
| 3,921,066 | 11/1975 | Angel et al. | 324/71 CP |
| 3,946,309 | 3/1976 | Roughton et al. | 324/30 R X |
| 4,045,725 | 8/1977 | Miller | 324/30 B |
| 4,119,909 | 10/1978 | Deberry | 324/30 B X |

OTHER PUBLICATIONS

Lawrence, James F., *Journal of Chromatography*, vol. 128, No. 1, Nov. 17, 1976, pp. 154–156.
Optichrom TM/LC System, Applied Automation Catalog.

*Primary Examiner*—Gerard R. Strecker

[57] ABSTRACT

A circuit is provided for producing an electrical output signal representative of the conductivity of a sample of fluid in a chromatograph sample cell. A constant A.C. current source is connected to one of the electrodes in the conductivity cell and a change in the resistivity of the cell is measured to produce an A.C. signal which is then conditioned by a signal conditioner. The signal conditioner scales the AC signal and converts it to a D.C. signal representing the resistivity of the conductivity cell. The resistivity signal is supplied to dividing means which is operable for inverting the resistivity signal to provide a signal representative of the conductivity of the sample fluid. Conductivity values can be detected in both the sample conductivity cell and a reference conductivity cell to provide conductivity signals for both the sample cell and the reference cell. These conductivity signals can be used for inputs into a difference amplifier to provide a signal representative of the difference between the two conductivity signals and its sign.

27 Claims, 4 Drawing Figures

CONSTANT ALTERNATING CURRENT CONDUCTIVITY DETECTOR FOR A CHROMATOGRAPH

The present invention relates to a circuit for producing an electrical output signal which is representative of the conductivity of a sample of fluid passing through a conductivity cell and a method of operating the conductivity cell. A reference cell can also be provided to produce a reference conductivity signal which can then be compared to the sample conductivity signal to provide other signals useful in controlling a process.

In chromatography, and more specifically, liquid chromatography, specific electrolytes in a solution are admitted to a column and are eluted sequentially therefrom. The concentrations of the electrolytes are determined on the basis of their respective conductivities. Many circuits are known in the art for providing conductivity output signals and have been effective in their operation. The present invention provides circuitry for determining such conductivities and provides an advance in the art of such circuitry.

An alternating current of a substantially constant magnitude is continuously applied to a sample cell and, optionally, to a standard or reference cell. The sample cell contains a stream comprising a carrier fluid plus elutes and the standard cell contains the carrier fluid. The circuit is operable for measuring the change in resistivity across the cells, i.e., the resistivity of the samples in the respective cells, and provides output signals each representative of the conductivity of the respective fluid in each of the sample cell and the standard cell. Under constant AC current conditions, the conductivity of the solution in each cell can be determined by generating an analog signal representative of the reciprocal of the solution resistivity which in turn is a function of the voltage drop across each of the cells. The use of a constant AC current to the conductivity cells has now been found to be highly advantageous. For low cell resistivity, cell polarization is reduced relative to a system using contact voltage. Also, for high cell resistivity the resistivity signal is greater than that for constant voltage systems and thereby increases the signal to noise ratio. The circuit of this invention has provisions for operation in a differential mode or in a single cell mode with a suitable variable current reference or with temperature compensation. There is also provision for generating the ratio of sample cell conductivity to standard cell conductivity. The conductivity is that of the fluid in a sample cell and a standard cell but is referred to in the art as sample cell conductivity and standard cell conductivity.

An object of this invention is to provide a circuit operable for producing an electrical output signal representative of the conductivity of the fluid in a chromatographic sample cell using constant AC current to the sample cell. Another object is to provide a circuit which has both a sample cell and a reference cell with the circuit being adapted for providing electrical output signals representative of the conductivities of the fluid in each of the sample cell and the reference cell. Another object is to provide a circuit which has means for providing an output signal representative of the difference between the conductivity of the fluid in the reference cell and the fluid in the sample cell and the sign of the signal. Another object is to provide a circuit which can provide a ratio of conductivities of the fluid in a sample cell and the fluid in a reference cell. A further object is to provide a circuit which can provide absolute values of cell conductivities and resistivities. A still further object is to provide a circuit with means for providing a constant AC current to both the sample cell and the reference cell. A still further object is to provide a circuit which is well adapted for its intended use.

Other objects and advantages of the present invention will become apparent from the following detailed description taken in connection with the accompanying drawings wherein are set forth by way of illustration and example, certain embodiments of this invention.

Figure 1:
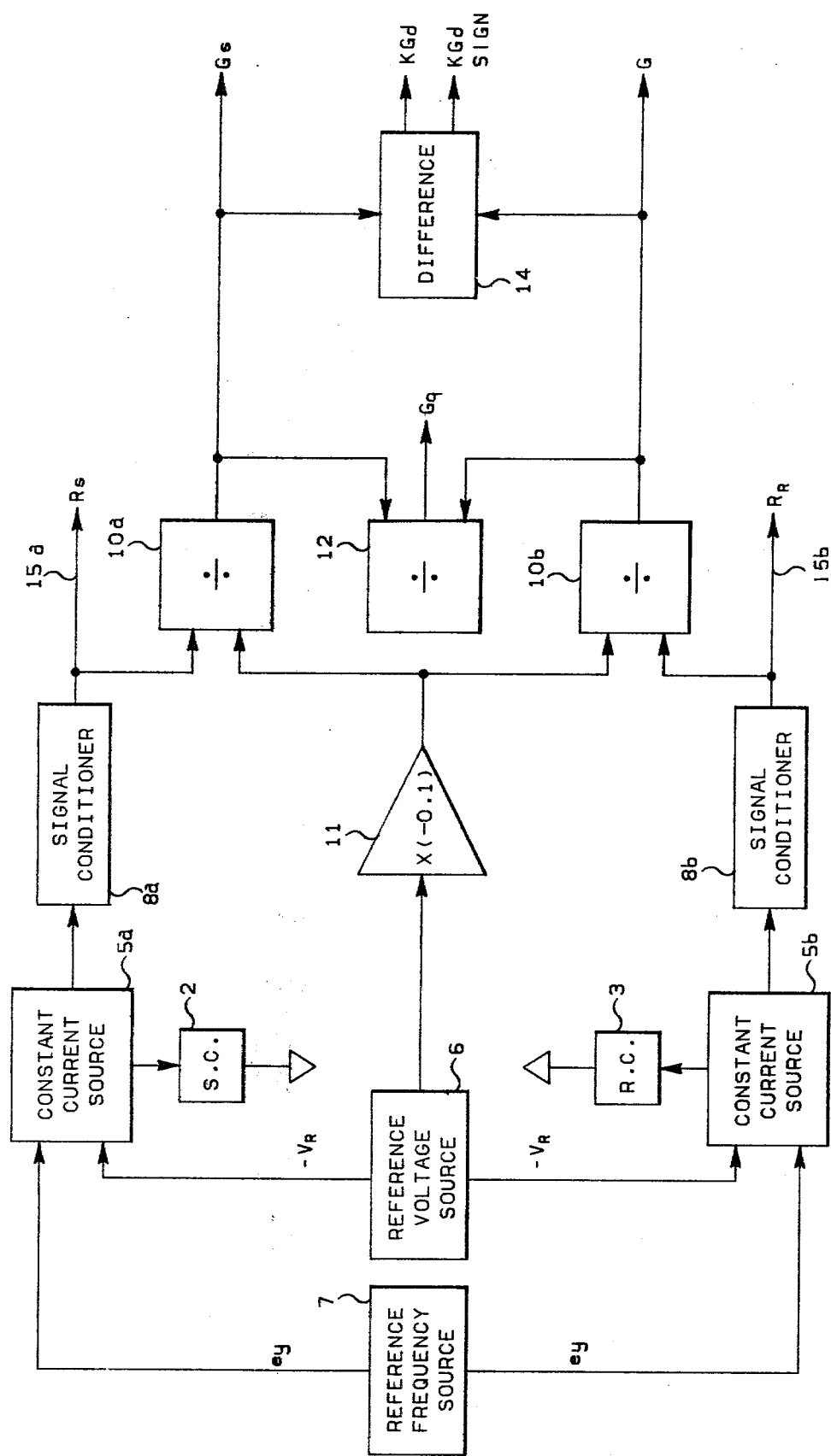
FIG. 1 is a block diagram of a circuit operable for providing a signal representative of the conductivity of a plurality of conductivity cell.

The reference numeral 1 designates generally a circuit operable for producing an electrical output signal representative of the conductivity of the fluid in one or more chromatographic conductivity cells such as conductivity cells 2 and 3. Means 5 is provided for supplying a constant AC current to each of the conductivity cells. There is connected to the means 5 a reference voltage source 6 and a reference frequency source 7. The means 5 each has an output signal representative of the resistivity of the respective cell 2 or 3 which are input signals to signal conditioners 8 which convert the AC output signals to a DC signal also representative of the resistivity of the respective cells 2 and 3. As noted herein, reference numerals without subscripts are used to represent parts which can be more than one in number. Therefore, reference numerals with a subscript indicate the same part as a described part having the same reference numeral without the subscript or a different subscript. This is done for purposes of clarity in the description of the circuit since various components are similar in operation and construction. Dividing means 10 is electrically connected to each of signal conditioners 8a and 8b. The divider means 10a and 10b are also electrically connected to a reference voltage source 11 which has an output voltage into which the resistivity signals from the signal conditioners 8a and 8b are divided to provide respective signals which are representative of the conductivities of the fluid in the respective cells 2 and 3 and in contact with the respective cell electrodes. A divider 12 is electrically connected to the divider means 10a and 10b and is operable for receiving the conductivity values $G_s$, representative of the conductivity of the fluid in sample cell 2, and $G_r$, representative of the conductivity of fluid in the reference cell 3 and dividing $G_s$ by $G_r$ to provide a ratio signal $G_q$. Hereinafter, the conductivities of fluids in the cells will be referred to a cell conductivity. The signals $G_s$ and $G_r$ are input signals to means 14 such as a difference amplifier means electrically connected to the dividers 10a and 10b. The means 14 is operable for subtracting the conductivity of the reference cell, $G_r$, from the conductivity of the sample cell, $G_s$, to provide an absolute value difference between the two signals. Also, the means 14 is operable for providing the sign of the signal. Output terminals 15a and 15b can be provided for the signal conditioners 8a and 8b, respectively, so that the resistivity of the respective cells 2 and 3 can be measured at the terminals 15a and 15b.

Figure 2A:
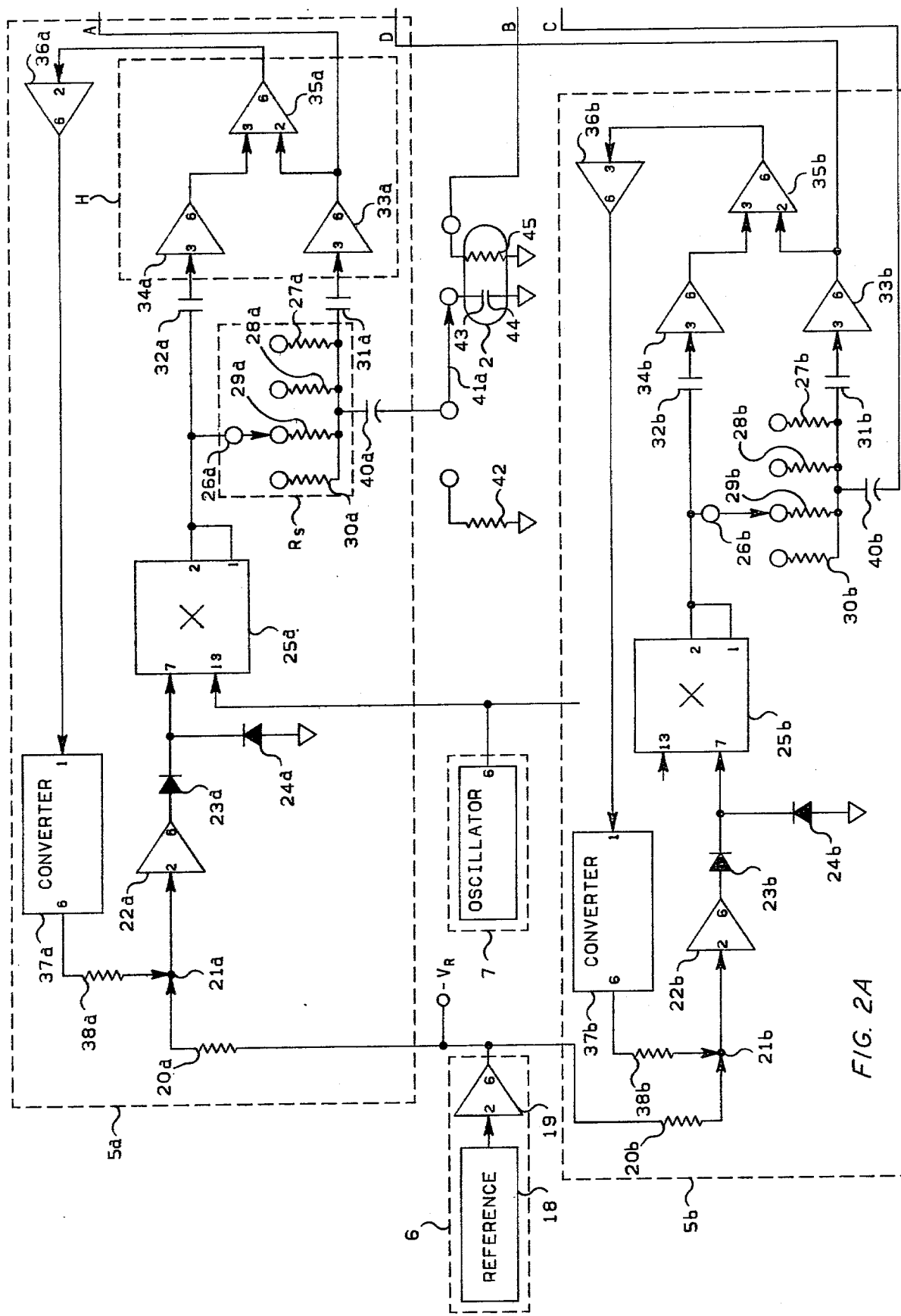
FIGS. 2A and 2B are a detailed schematic of the circuit illustrated in FIG. 1.
Figure 2B:
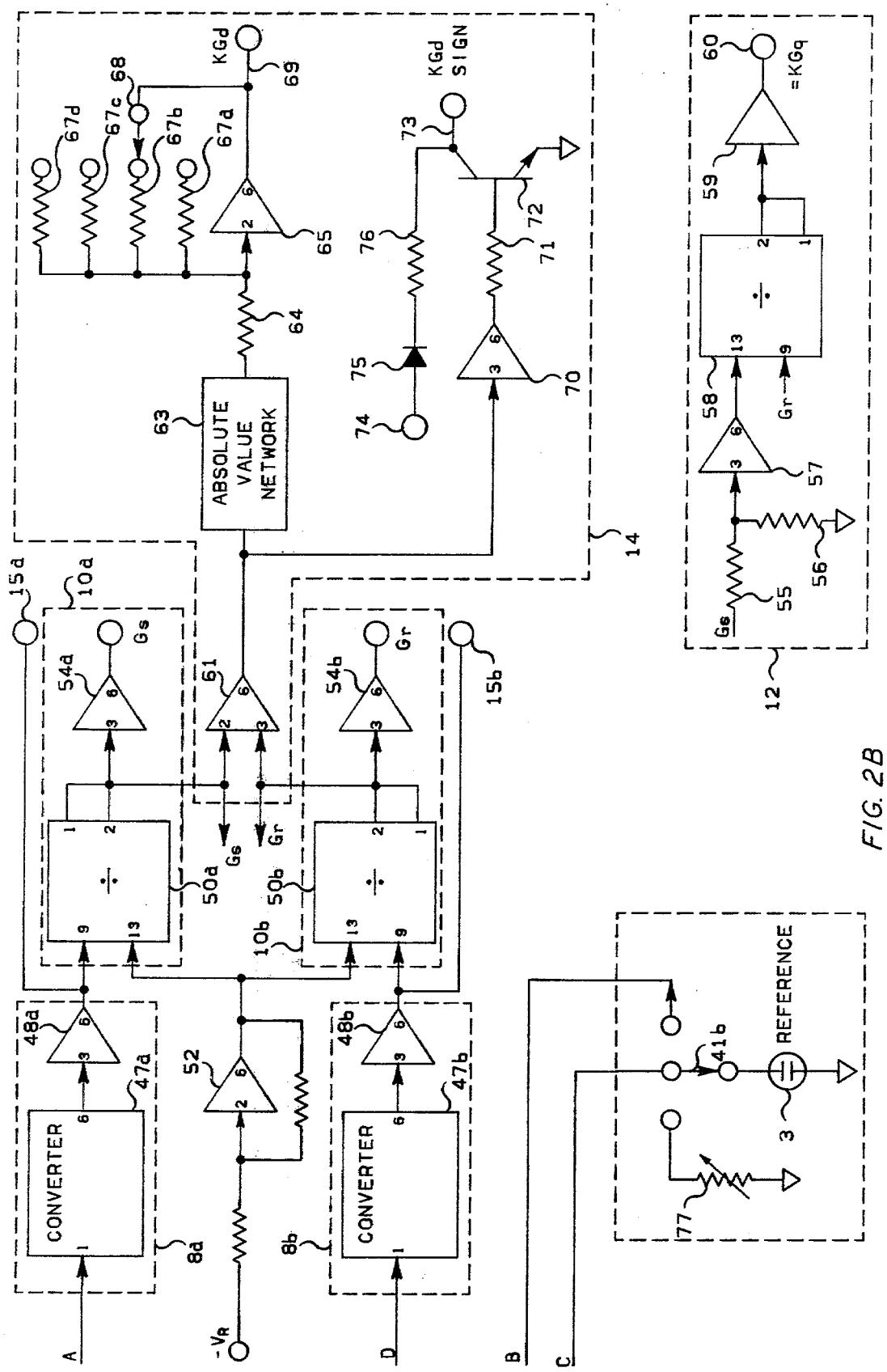

FIG. 2 is a schematic illustration of the various component parts making up the circuit shown generally in FIG. 1. The various portions of the circuit as described above and illustrated in FIG. 1 are shown in broken line outlines in FIG. 2.

In the description below as it relates to amplifiers, pin 2 is an inverting input, pin 3 is a noninverting input and pin 6 is the output.

The reference voltage source 6 in the illustrated circuit includes a substantially constant DC voltage reference source 18 which is electrically connected to a unity gain inverting operational amplifier 19 at pin 2. The output of the amplifier 19 is at pin 6 which is electrically connected to the constant current source 5. The output from the pin 6 of the amplifier 19 is electrically connected to one terminal of a resistor 20 and the other terminal of the resistor 20 is electrically connected to a summing junction 21 which is pin 2 of an inverting amplifier 22. Output pin 6 of the amplifier 22 is electrically connected to the anode of a diode 23 and the cathode of the diode 23 is electrically connected to a cathode of another diode 24 and the anode of the diode 24 is connected to common. The cathode of the diode 23 is connected to a first input pin 7 of a multiplier 25 so that the amplifier 22 has its output received by the multiplier 25.

Figure 3:
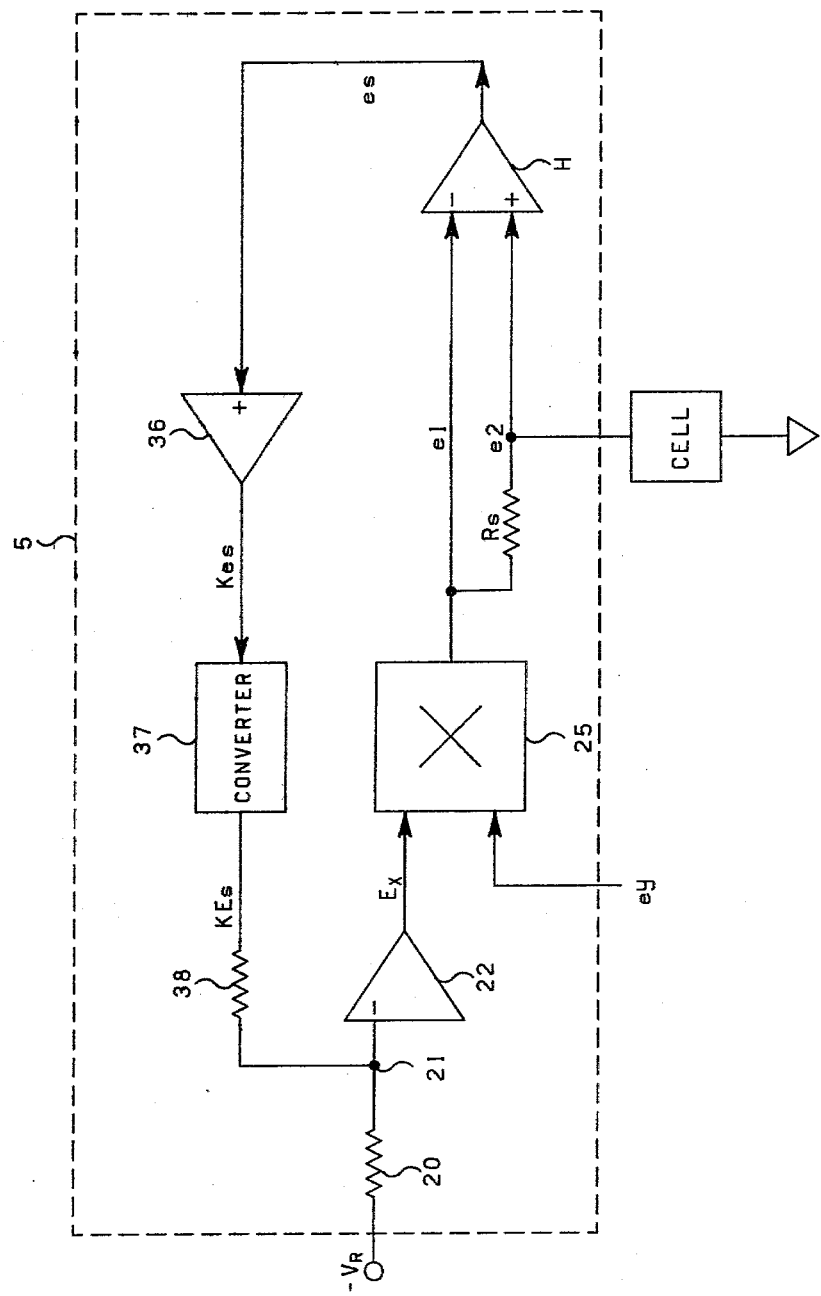
FIG. 3 is a simplified schematic of a constant current source portion of the schematic of FIG. 1.

The reference frequency source 7 preferably is an oscillator and has the output pin 6 thereof electrically connected to a second input pin 13 of the multiplier 25. The output pins 1 and 2 of the multiplier 25 are electrically connected together to produce the output signal of the multiplier 25 and are connected to one pole or common terminal of a switch 26. The switch 26 preferably is of a selector type and has the common pole thereof selectively movable between selectable terminals and thereby electrical connection with a respective terminal of any one of a plurality of parallel connected resistors 27, 28, 29 and 30 each of which has a different resistance. This provides an operating range adjustment for the circuit to compensate for cell constants of other than 1. For example, the resistors 27, 28, 29 and 30 are one magnitude of resistance different, for example, the resistor 27 can be 1 ohm, the resistor 28 can be 10 ohms, the resistor 29 can be 100 ohms and the resistor 30 can be 1,000 ohms. The other terminals of the resistors 27-30 are electrically connected together and are electrically connected to a capacitor 31. The arrangement of resistors 27, 28, 29 and 30 is one embodiment of the resistor means $R_s$ of FIG. 3. The pins 1 and 2 of the multiplier 25 are electrically connected to a capacitor 32. The capacitors 31 and 32 have the other terminals thereof each connected to a respective amplifier 33 and 34 at the respective input pin 3 thereof. The amplifiers 33 and 34 serve as buffer amplifiers. The outputs of the amplifiers 33 and 34, at the respective pin 6 are electrically connected to a differential amplifier 35. The arrangement of amplifiers 33, 34 and 35 is one embodiment of the amplifier means H in FIG. 2 and FIG. 3. The pin 6 of the amplifier 33 is electrically connected to input pin 2 of the amplifier 35 while the pin 6 of the amplifier 34 is electrically connected to input pin 3 of the amplifier 35. Output pin 6 of the amplifier 35 is electrically connected to the noninverting input of a buffer amplifier 36. The output of the amplifier 36 is electrically connected to input pin 1 of a converter 37 which is operable for converting A.C. to D.C. The output terminal 6 of the converter 37 is electrically connected to the inverting input of amplifier 22 through a resistor 38. The amplifier 36, converter 37 and resistor 38 provides a D.C. feedback to the amplifier 22 for stabilization.

Resistors 27 through 30, inclusive, are electrically connected to one terminal of a capacitor 40 which in turn has its other terminal electrically connected to a selector switch 41. The switch 41 is operable for selecting a calibration circuit which, via a resistor 42, provides an electrical connection to common. In the operation mode, the switch 41a selectively provides a circuit to the sample conductivity cell 2. One terminal of the switch 41 is electrically connected to the electrode 43a of the sample cell while the other electrode 44 is electrically connected to common. A temperature compensating thermistor 45 can be selected by the switch 41b in place of the reference cell 3 to compensate for temperature variations of the sample in the cell 2. The thermistor 45 is selectively made a part of the circuit by operation of the switch 41b which has one terminal of the thermistor 45 electrically connected to one of its selectable terminals. The other terminal of the thermistor 45 is connected to common. The thermistor 45 selectively replaces the reference cell 3 in the circuit by action of switch 41b. The resistance Rs, capacitor 40a, and sample conductivity cell 2 provide an AC resistive network which, in accordance with Ohms law, produces an AC signal at the junction of Rs and capacitor 40a which is representative of the resistivity of the fluid in conductivity cell 2. The constant current means 5 described above provides a circuit which senses a change in the resistivity between the electrodes 43 and 44 and provides an AC output signal representative thereof to the signal conditioner 8.

The signal conditioner 8 is operable for changing the AC output signal available at the output of the amplifier 33 to a DC signal and also preferably multiplies the converted signal by 2 to provide a maximum 10 volt output. In the illustrated structure, the signal conditioning means 8 includes a converter 47 which has output pin 1 electrically connected to the output of the amplifier 33. The output pin 6 of the converter 47 is electrically connected to an X2 buffer amplifier 48 at output pin 3. The terminal 15 is connected to output pin 6 of amplifier 48 and provides a terminal for obtaining a signal representative of the resistivity across the electrodes 43 and 44. The amplifier 48 at the output pin 6 provides an output signal to a divider 50 by being electrically connected to input pin 9 of the divider 50. The divider 50 is operable to provide a reciprocal of the resistivity signal from output pin 6 of the amplifier 48 to give a signal representative of the conductivity of the respective cell 2 or 3.

The conductivity signal can be advantageously provided by having a reference voltage source electrically connected to the divider 50 at input pin 13. This can be accomplished by having the voltage source 6 electrically connected to an input pin 2 of an inverting amplifier 52. The output pin 6 of amplifier 52 is electrically connected to the input 13 of the divider 50 and preferably supplies one volt DC to the divider 50. By dividing one volt DC from the amplifier 52 by the D.C. voltage representing the measured resistivity of the respective cell 2 or 3 from the amplifier 48, conductivity signals can be provided. Output pins 1 and 2 of the divider 50 are electrically tied together and are electrically connected to input pin 3 of a buffer amplifier 54. The output of the buffer amplifier 54 is its pin 6 and is representative of the conductivity of the respective cell 2 or 3. The conductivity signal of the sample cell 2 is designated $G_s$ while the conductivity signal of the reference cell is designated $G_r$.

The dividing means 12 is operable for supplying a signal representative of the ratio of the conductivity of the sample cell 2 to the conductivity of the reference cell 3. In the illustrated structure, the dividing means 12 includes a resistor 55 having one terminal electrically connected to pins 1 and 2 of the divider 50a and is operable for receiving the conductivity signal $G_s$. The resistor 55 has its other terminal electrically connected to one terminal of resistor 56 which has its other terminal electrically connected to common. The other terminal of the resistor 55 is also electrically connected to a buffer amplifier 57 at input pin 3. The signal received by the amplifier 57 is preferably about 0.1 $G_s$. The output of the amplifier 57 is available at its output pin 6 which is electrically connected to a divider 58 at its pin 13. The conductivity signal $G_r$ is available from the divider 50b which has its output pins 1 and 2 electrically connected to input pin 9 of the divider 58. The divider 58 acts on the signals $G_s$ and $G_r$ by dividing $G_s$ by $G_r$ to provide an output signal at the output pins 1 and 2 of the divider 58, which are electrically tied together and electrically connected to input pin 3 of a buffer amplifier 59. An output of buffer amplifier 59 is available at its output pin 6 which is electrically connected to a terminal 60 for measuring or otherwise using the ratio $G_s/G_r$, which is signal $G_q$.

The means 14 in the illustrated structure is operable for providing a signal, $G_d$, which is the difference between $G_s$ and $G_r$. The means 14 provides an absolute value of the difference signal $G_d$ and its sign (polarity). The sign of such difference signal is indicative of the relative amplitude of $G_s$ with respect to $G_r$, i.e., if the sign is negative, $G_s$ is larger than $G_r$ and vice versa. In the illustrated circuit, a differential amplifier 61 has its input pin 2 electrically connected to output pins 1 and 2 of the divider 50a and pin 3 electrically connected to pins 1 and 2 of the divider 50b. The output from the amplifier 61 is at its output pin 6 which is electrically connected to input pin 2 of an absolute value network 63 which is operable for converting input signals of either polarity to positive signals. Suitable absolute value networks are taught in "Applications of Operational Amplifiers", Jerald D. Graeme, Burr Brown Research Corp., published by McGraw-Hill Co., 1973, at pages 119-132 and "Application Manual for Computing Amplifiers", Philbrick Researchers, Inc., published by George A. Philbrick Researchers, Inc., 1966, at page 59 which disclosures are incorporated herein by reference. The output pin 6 of the network 63 is electrically connected to one terminal of a resistor 64. The other terminal of the resistor 64 is electrically connected to input pin 2 of an inverting amplifier 65. The output pin 6 of the amplifier 65 is electrically connected to a terminal 69 for providing the signal $KG_d$, which is equal to $K(G_s$ minus $G_r)$. The other terminal of the resistor 64 is also electrically connected to a plurality of feedback resistors 67a, 67b, 67c and 67d each of which has one terminal electrically connected together and to the terminal of the resistor 64. The other terminal of each of the resistors is connected to a respective selectable terminal of a selector switch 68 which is used for gain (K) selection of amplifier 65. By proper selection of the appropriate resistor, a K of, e.g., 1, 5, 10 or 20 can be realized. The switch 68 has the common terminal thereof electrically connected to the terminal 69.

The means 14 further includes a buffer amplifier 70 which has its pin 3 electrically connected to output pin 6 of the amplifier 61. The output pin 6 of the amplifier 70 is electrically connected to one terminal of a resistor 71 which has the other terminal thereof electrically connected to the base terminal of a transistor 72 which is operable to provide drive current to a light emitting diode (LED) 75. The emitter terminal of the transistor 72 is electrically connected to common while the collector terminal of the transistor 72 is electrically connected to a terminal 73 at which a signal representative of the sign of the values of $G_d$ is available. A voltage source 74 is electrically connected to the terminal 73 by having the LED 75 and a resistor 76 electrically connected in series therebetween with the LED being electrically connected between the resistor 76 and the voltage source 74. These serve the respective functions of indicating that the transistor 72 is an on/off state and current limiting.

In the illustrated structure, the switch 41b has electrically connected to one terminal thereof available a resistance means 77 which is operable to provide a variable micromho reference conductance source in the absence of reference cell 3. With this arrangement, a reference conductance of, for example, 1 micromho to 999 micromho can be provided in lieu of the reference cell conductance.

The present invention can be more fully understood by a description of the operation thereof. The following discussion is depicted circuit-wise in FIGS. 2 and 3. By virtue of being connected in series with the variable conductance of the sample cell 2, the resistor means $R_s$ senses the current passing through the sample cell 2. The series circuit comprising $R_s$ and sample cell 2 has variable A.C. voltage $e_1$ applied thereto. $e_1$ is derived from the multiplier 25 and is proportional to the product of: (1) an AC voltage, $e_y$ from the oscillator 7 and (2) a DC voltage $E_x$. $E_x$ is equal to the inverted summation of $-V_R$ and $KE_s$ from converter 37. Since $-V_R$ is derived from a precision reference source, it is a constant and $E_x$ is therefore inversely proportional to $KE_s$ which in turn is directly proportional to $e_s$ which is equal to $e_1$ minus $e_2$. The voltage $e_2$ is directly proportional to the resistivity R of the conductivity cell 2 or 3. If R increases, $e_2$ increases, etc. As $e_2$ decreases, as for example, the difference ($e_s$) between $e_1$ and $e_2$ tends to increase also but the circuit acts to reduce $e_1$ and thereby maintain $e_s$ constant. An increase in $e_s$ is corrected by a decrease in $e_1$, etc. Variations of $e_y$ from oscillator 7 are similarly corrected for. An increase in $e_y$, say, would tend to increase $e_1$ which in turn would mean an increase in $e_s$ which is corrected for as above.

Thus, it can be seen that as the resistivity of the fluid in the sample cell 2 or reference cell 3 changes, $e_{2a}$ or $e_{2b}$ change respectively and are thus directly representative of the resistivity and inversely representative of their respective cell's conductivity. Further use of $e_{2a}$ and $e_{2b}$ is made in determining: (1) the difference in conductivity between that of the reference 3 and that of the sample cell 2, (2) the conductivity ratio of the cells, (3) the absolute conductivity of each of said cells, and (4) the resistivity of said cells.

The following are components which can be used in the above-described circuit:

| | |
|---|---|
| Variable Resistor | Allied Electronics, Cat. No. 753-7840 |

| | | |
|---|---|---|
| Multiplier 25 | Analog Devices, Inc., AD 532 | |
| Divider 50, 58 | Burr-Brown, Inc., BB4291J | |
| Differential Amplifier 35 & 61 | Burr-Brown, Inc., BB3627 | |
| Operational Amplifiers. 22, 65, and 70 | Precision Monlithics, Inc., OP 10EY | |
| All other operational amplifiers | Motorola, Inc., MC1458 | |
| Oscillator 7 | Burr-Brown, Inc., BB4423 | |
| Reference voltage source 18 | Analog Devices, Inc., AD2700L/U | |
| Conductivity Cells 2, 3 | Leed's & Northrup 4905-1-33-088-7 | |

It is to be understood that while there has been illustrated and described certain forms of this invention, it is not to be limited to the specific form or arrangement of parts herein described and shown except to the extent that such limitations are found in the claims.

What is claimed and desired to be secured by Letters Patent is:

1. A circuit for producing an electrical output signal representative of the conductivity of a sample of fluid, including:
   a first conductivity cell having first and second spaced apart electrodes adapted for contact with a first fluid sample;
   a first reference DC potential source;
   a reference frequency source;
   first means having a first electrical input from said first reference DC potential source and a second electrical input from said reference frequency source and being operable for multiplying the first reference DC potential with the reference frequency to provide a constant AC current output to said first electrode of said first conductivity cell and for producing a first signal representative of the resistivity of fluid in said first conductivity cell;
   second means electrically connected to said first means and operable for receiving said first signal and converting the first signal to a DC second signal representative of the resistivity of the first fluid in the first conductivity cell;
   a second reference DC potential source for generating a second reference DC potential; and
   first dividing means electrically connected to said second means and to said second reference DC potential source and operable for dividing the second reference DC potential by the DC second signal to provide a third signal representative of the conductivity of the first fluid in said first conductivity cell.

2. A circuit as set forth in claim 1 including:
   a second conductivity cell having third and fourth spaced apart electrodes adapted for contact with a second fluid sample;
   fourth means electrically connecting said first reference DC potential source and said reference frequency source to said third electrode of the second conductivity cell and being operable for providing a constant AC current to said third electrode and produce a fourth signal representative of the resistivity of second fluid in the second conductivity cell;
   fifth means electrically connected to said fourth means and operable for receiving said fourth signal and converting the fourth signal to a DC fifth signal representative of the resistivity of the second fluid in the second conductivity cell; and
   second dividing means electrically connected to said fifth means and second reference potential source and operable for dividing the second reference potential by the fifth signal to provide a sixth signal representative of the conductivity of the second fluid in the second conductivity cell.

3. A circuit as set forth in claim 2 including:
   sixth means electrically connected to said first and second dividing means and operable for subtracting the sixth signal from the third signal to provide a seventh signal and its sign.

4. A circuit as set forth in claim 3 including:
   third dividing means electrically connected to said first and second dividing means and operable for dividing the third signal by the sixth signal to provide a quotient eighth signal.

5. A circuit as set forth in claim 2 including:
   third dividing means electrically connected to said first and second dividing means and operable for dividing the third signal by the sixth signal to provide a quotient eighth signal.

6. A circuit as set forth in claims 1, 2, 3, 4, or 5, wherein said first means includes:
   first inverting amplifier with said first reference potential source being electrically connected to an input terminal thereof;
   a multiplier having first and second input terminals and an output terminal, said reference frequency source and an output terminal of said first inverting amplifier being electrically connected to respective input terminals of said multiplier, said multiplier being operable for providing an output at said output terminal of the multiplier representative of the multiplication product of the outputs of the first inverting amplifier and the reference frequency source;
   means electrically connecting said first electrode of the first conductivity cell to said output terminal of said multiplier; and
   feedback means electrically connecting said output terminal of the multiplier to the input terminal of the first inverting amplifier.

7. A circuit as set forth in claim 6 wherein said first means further includes:
   a first diode having an anode electrically connected to said output terminal of the inverting amplifier and having a cathode electrically connected to an input terminal of said multiplier whereby said first diode effects said electrical connection of the inverting amplifier to said multiplier;
   a second diode having a cathode electrically connected to the cathode of the first diode and having an anode electrically connected to common; and
   a resistor means electrically connecting the output terminal of the multiplier to said first electrode of the first conductivity cell.

8. A circuit as set forth in claim 7 wherein said first means further includes:
   a first buffer amplifier having an input terminal electrically connected to said output terminal of said multiplier and having an output terminal;
   a second buffer amplifier having an input terminal electrically connected to said one electrode of the first conductivity cell between said resistor means and said one electrode of the first conductivity cell and having an output terminal;
   a first differential amplifier having input terminals each electrically connected to a respective output terminal of the first and second buffer amplifiers and having an output terminal; and a converter having an input terminal electrically connected to said output terminal of the first differential amplifier and having an output terminal electrically connected to said input terminal of the first inverting amplifier.

9. A circuit as set forth in claim 8 wherein said first means further includes:

a first resistor electrically connected between said output terminal of the converter and the input terminal of the first inverting amplifier;

a second resistor electrically connected between the first reference DC potential source and the input terminal of the first inverting amplifier; and a third buffer amplifier electrically connected between said first differential amplifier and said converter by having an input terminal of the third buffer amplifier electrically connected to the output terminal of the first differential amplifier and having an output terminal of the third buffer amplifier electrically connected to said input terminal of the converter.

10. A circuit as set forth in claim 9 wherein said resistor means includes:

a selector switch having a common terminal and a plurality of selectable terminals said common terminal being electrically connected to said output terminal of the multiplier;

a plurality of third resistors in parallel arrangement each having one end electrically connected to a respective said selectable terminal and the other ends of the third resistors electrically connected together said third resistors each having a resistance different than the resistance of the other third resistor.

11. A circuit as set forth in claims 2, 3, 4, or 5, wherein said fourth means includes:

first inverting amplifier with said first reference potential source being electrically connected to an input terminal thereof;

a multiplier with said reference frequency source and an output terminal of said first inverting amplifier being electrically connected to respective input terminals of multiplier, said multiplier being operable for providing an output at an output terminal of the multiplier representative of the product of the outputs of the first inverting amplifier and reference frequency source;

means electrically connecting said one electrode of the first conductivity cell to said output terminal of said multiplier; and feedback means electrically connecting said output terminal of the multiplier to the input terminal of the first inverting amplifier.

12. A circuit as set forth in claim 11 wherein said fourth means further includes:

a first diode having an anode electrically connected to said output terminal of the inverting amplifier and has cathode electrically connected to an input terminal of said multiplier whereby said first diode effects said electrical connection of the inverting amplifier to said multiplier;

a second diode having a cathode electrically connected to the cathode of the first diode and having an anode electrically connected to common; and a resistor means electrically connecting the output terminal of the multiplier to one electrode of the first conductivity cell.

13. A circuit as set forth in claim 12 wherein said fourth means further includes:

a first buffer amplifier having an input terminal electrically connected to said output terminal of said multiplier and having an output terminal;

a second buffer amplifier having an input terminal electrically connected to said one electrode of the first conductivity cell between said resistor means and said one electrode of the first conductivity cell and having an output terminal;

a first differential amplifier having input terminals each electrically connected to a respective output terminal of the first and second buffer amplifiers and having an output terminal; and a converter having an input terminal electrically connected to said output terminal of the first differential amplifier and having an output terminal electrically connected to said input terminal of the first inverting amplifier.

14. A circuit as set forth in claim 13 wherein said fourth means further includes:

a first resistor electrically connected between said output terminal of the converter and the input terminal of the first inverting amplifier;

a second resistor electrically connected between the first reference DC potential source and the input terminal of the first inverting amplifier; and a third buffer amplifier electrically connected between said first differential amplifier and said converter by having an input terminal of the third buffer amplifier electrically connected to the output terminal of the first differential amplifier and having an output terminal of the third buffer amplifier electrically connected to said input terminal of the converter.

15. A circuit as set forth in claim 14 wherein said resistor means includes:

a selector switch having a common terminal and a plurality selectable terminals said common terminal being electrically connected to said output terminal of the multiplier;

a plurality of third resistors in parallel arrangement each having one end electrically connected to a respective selectable terminal and the other ends of the third resistors electrically connected together said third resistors each having a resistance different than the resistance of the other third resistor.

16. A circuit as set forth in claim 2 including:

a selector switch having a common terminal electrically connected to said fourth means and having a plurality of selectable terminals with one of said selectable terminals being electrically connected to said one electrode of the second conductivity cell whereby said selector switch being operable for selectively electrically connecting said fourth means to said one electrode of the second conductivity cell; and a variable resistor means electrically connected to another of the selectable terminals of the selector switch.

17. A method of operating a conductivity cell comprising:

contacting a first conductivity cell with a first fluid sample, said first conductivity cell having first and second spaced apart electrodes adapted for contact with a fluid sample;
generating a first reference DC potential;
generating a reference frequency;
multiplying the first reference DC potential with the reference frequency to provide a constant AC current output to the first electrode of the first conductivity cell;
generating a first signal representative of the resistivity of the fluid sample in the first conductivity cell; and
changing said first signal to a second signal representative of the conductivity of the fluid sample in the first conductivity cell.

18. A method as set forth in claim 17 including:
applying a substantially constant AC current to one electrode of a second conductivity cell containing a reference fluid sample;
generating a third signal representative of the resistivity of the reference fluid sample in the second conductivity cell;
changing said third signal to a fourth signal representative of the conductivity of the reference fluid sample in the second conductivity cell; and
subtracting the fourth signal from the second signal and providing a fifth signal representative of the difference and a sixth signal representative of the sign of the difference.

19. A method as in claim 17 further comprising:
converting the first signal representative of the resistivity of the fluid sample in the first conductivity cell to a DC second signal representative of the resistivity of the fluid sample in the first conductivity cell;
generating a second reference DC potential; and
dividing the second reference DC potential by the DC second signal to provide a third signal representative of the conductivity of the fluid in the first conductivity cell.

20. A circuit for producing an electrical output signal representative of the conductivity of a sample of fluid, including:
a first conductivity cell;
first means electrically connected to said first conductivity cell for applying a substantially constant AC current to one electrode of the first conductivity cell containing a fluid sample;
second means electrically connected to said first conductivity cell for generating a first signal representative of the resistivity of the fluid sample in the first conductivity cell;
third means electrically connected to said second means for changing said first signal to a second signal representative of the conductivity of the fluid sample in the first conductivity cell; and
wherein said first means for applying a substantially constant AC current further includes:
a first reference DC potential source;
a reference frequency source; and
means having a first electrical input from said first reference DC potential source and a second reference input from said reference frequency source and being operable for multiplying the first reference DC potential with the reference frequency to provide a constant AC current output.

21. A circuit as in claim 20 including:
a second conductivity cell;
fourth means electrically connected to said second conductivity cell for applying a substantially constant AC current to one electrode of the second conductivity cell containing a reference fluid sample;
fifth means electrically connected to said second conductivity cell for generating a third signal representative of the resistivity of the reference fluid sample in the second conductivity cell;
sixth means electrically connected to said fifth means for changing said third signal to a fourth signal representative of the conductivity of the reference fluid sample in the second conductivity cell; and
seventh means electrically connected to the sixth means and third means for subtracting the fourth signal from the second signal and providing a fifth signal representative of the difference and a sixth signal representative of the sign of the difference.

22. A circuit as set forth in claim 20 wherein said third means further comprises:
a second reference DC potential source for generating a second reference DC potential; and
first dividing means electrically connected to said second means and to said second reference DC potential source and operable for dividing the second reference DC potential by the second signal to provide a third signal representative of the conductivity of the first fluid in the first conductivity cell.

23. A method for producing an electrical output signal representative of the conductivity of a sample of fluid, including:
contacting a first conductivity cell with a first fluid sample, said first conductivity cell having first and second spaced apart electrodes adapted for contact with a fluid sample;
generating a first reference DC potential;
generating a reference frequency;
multiplying the first reference DC potential with the reference frequency to provide a constant AC current output to the first electrode of the first conductivity cell;
producing a first signal representative of the resistivity of the fluid in the first conductivity cell;
converting the first signal to a DC second signal representative of the resistivity of the fluid in the first conductivity cell;
generating a second reference DC potential; and
dividing the second reference DC potential by the DC second signal to provide a third signal representative of the conductivity of the fluid in the first conductivity cell.

24. A method as in claim 23 further comprising:
contacting a second conductivity cell with a second fluid sample, said second conductivity cell having third and fourth electrodes adapted for contact with a fluid sample;
multiplying the first reference DC potential with the reference frequency to provide a constant current AC signal to the third electrode of the second conductivity cell;
producing a fourth signal representative of the resistivity of the second fluid in the second conductivity cell;
converting the fourth signal to a DC fifth signal representative of the resistivity of the second fluid in the second conductivity cell; and
dividing the second reference DC potential by the DC fifth signal to provide a sixth signal representative of the conductivity of the second fluid in the second conductivity cell.
25. A method as in claim 24 further comprising:
subtracting the sixth signal from the third signal to produce a second signal and its sign.
26. A method as in claim 24 further comprising: dividing the third signal by the sixth signal to provide a quotient eighth signal.
27. A method as in claim 25 further comprising:
dividing the third signal by the sixth signal to provide a quotient eighth signal.

* * * * *